(12) United States Patent
Kitaura (10) Patent No.: US 8,637,701 B2
(45) Date of Patent: Jan. 28, 2014

(54) METHOD FOR PRODUCING (METH) ACRYLIC ACID

(75) Inventor: Masatsugu Kitaura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 164 days.

(21) Appl. No.: 13/320,567

(22) PCT Filed: Apr. 30, 2010

(86) PCT No.: PCT/JP2010/057695
§ 371 (c)(1),
(2), (4) Date: Nov. 15, 2011

(87) PCT Pub. No.: WO2010/131589
PCT Pub. Date: Nov. 18, 2010

(65) Prior Publication Data
US 2012/0077947 A1    Mar. 29, 2012

(30) Foreign Application Priority Data

May 15, 2009  (JP) ................. 2009-119210

(51) Int. Cl.
*C07C 51/43* (2006.01)
(52) U.S. Cl.
USPC ...................................... 562/600
(58) Field of Classification Search
USPC ...................................... 562/600
See application file for complete search history.

(56) References Cited

U.S. PATENT DOCUMENTS

| | | | |
|---|---|---|---|
| 4,893,999 A | 1/1990 | Chmelir et al. |
| 4,920,202 A | 4/1990 | Irie et al. |
| 5,264,495 A | 11/1993 | Irie et al. |
| 5,275,773 A | 1/1994 | Irie et al. |
| 5,385,983 A | 1/1995 | Graham |
| 5,409,771 A | 4/1995 | Dahmen et al. |
| 5,462,972 A | 10/1995 | Smith et al. |
| 5,597,873 A | 1/1997 | Chambers et al. |
| 5,610,220 A | 3/1997 | Klimmek et al. |
| 5,633,316 A | 5/1997 | Garter et al. |
| 5,669,894 A | 9/1997 | Goldman et al. |
| 5,674,633 A | 10/1997 | Saunders et al. |
| 6,164,455 A | 12/2000 | Kakita et al. |
| 6,207,796 B1 | 3/2001 | Dairoku et al. |
| 6,241,928 B1 | 6/2001 | Hatsuda et al. |
| 6,291,636 B1 | 9/2001 | Miyake et al. |
| 6,444,744 B1 | 9/2002 | Fujimaru et al. |
| 6,472,478 B1 | 10/2002 | Funk et al. |
| 6,503,979 B1 | 1/2003 | Funk et al. |
| 6,710,141 B1 | 3/2004 | Heide et al. |
| 6,867,269 B2 | 3/2005 | Sakamoto et al. |
| 6,875,511 B2 | 4/2005 | Dairoku et al. |
| 6,906,159 B2 | 6/2005 | Dairoku et al. |
| 6,987,151 B2 | 1/2006 | Gartner et al. |
| 7,091,253 B2 | 8/2006 | Dairoku et al. |
| 7,332,635 B2 | 2/2008 | Iikubo et al. |
| 7,342,130 B2 | 3/2008 | Shibusawa et al. |
| 2004/0186229 A1 | 9/2004 | Heide et al. |
| 2005/0215734 A1 | 9/2005 | Dairoku et al. |
| 2005/0221457 A1 | 10/2005 | Tsobanakis et al. |
| 2006/0281947 A1* | 12/2006 | Yada et al. ............ 562/600 |
| 2007/0129572 A1 | 6/2007 | Shibusawa et al. |
| 2007/0238898 A1 | 10/2007 | Matsumoto |
| 2008/0004408 A1 | 1/2008 | Stueven et al. |
| 2009/0076284 A1* | 3/2009 | Heilek et al. ............ 548/540 |
| 2009/0298144 A1 | 12/2009 | Tsobanakis et al. |
| 2010/0069583 A1 | 3/2010 | Kasuga et al. |

FOREIGN PATENT DOCUMENTS

| | | |
|---|---|---|
| CA | 2319786 | 8/1999 |
| CN | 1234407 | 11/1999 |
| EP | 0 450 923 | 10/1991 |
| EP | 0 450 924 | 10/1991 |
| EP | 0 349 240 | 1/1993 |
| EP | 0 605 150 | 7/1994 |
| EP | 0 668 080 | 8/1995 |
| EP | 0 812 873 | 12/1997 |
| JP | 7-224304 | 8/1995 |
| JP | 7-242709 | 9/1995 |
| JP | 2005-521718 | 7/2005 |
| JP | 2007-182437 | 7/2007 |
| JP | 2007-277182 | 10/2007 |
| JP | 2008-115103 | 5/2008 |
| WO | 99/42494 | 8/1999 |
| WO | 99/42496 | 8/1999 |
| WO | 99/43720 | 9/1999 |
| WO | 01/16346 | 3/2001 |
| WO | 01/38402 | 5/2001 |
| WO | 2005/016393 | 2/2005 |
| WO | 2005/095320 | 10/2005 |
| WO | 2006/034806 | 4/2006 |
| WO | 2006/087084 | 7/2006 |
| WO | 2006/087083 | 8/2006 |
| WO | 2007/106100 | 9/2007 |
| WO | 2008/027742 | 3/2008 |
| WO | 2008/114745 | 9/2008 |

OTHER PUBLICATIONS

International Search Report issued Jun. 1, 2010 in International (PCT) Application No. PCT/JP2010/057695 of which the present application is the national stage.
Office Action issued Jun. 18, 2013 in corresponding Chinese Application No. 201080017755.2, with English translation thereof.

* cited by examiner

*Primary Examiner* — Brian J Davis
(74) *Attorney, Agent, or Firm* — Wenderoth, Lind & Ponack, L.L.P.

(57) ABSTRACT

A method for efficiently producing (meth)acrylic acid by crystallization using a plurality of crystallizers to purify (meth)acrylic acid and a refrigerator for supplying both of a cooling medium and a heating medium, while the refrigerator is stably operated for supplying media having a proper temperature and the temperature of the crystallizers is maintained.

9 Claims, 2 Drawing Sheets

METHOD FOR PRODUCING (METH) ACRYLIC ACID

TECHNICAL FIELD

The present invention relates to a method for producing (meth)acrylic acid.

BACKGROUND ART (Meth)acrylic acid is generally produced by carrying out a gas-phase catalytic oxidation reaction to obtain a gas containing (meth)acrylic acid, supplying the gas into a condensation column or a collection column to obtain a crude (meth)acrylic acid solution, and purifying (meth)acrylic acid from the crude solution. The procedure for such a purification is exemplified by crystallization in addition to distillation, diffusion, extraction and others.

In general, crystallization of (meth)acrylic acid from a crude solution is carried out in two stages. First, (meth)acrylic acid is crystallized by cooling and the liquid portion is removed. Next, the obtained (meth)acrylic acid crystal is melted to be transported to the next step. In order to further improve the purity of a crystal, a sweating step may be carried out before the melting step in some cases. In the sweating step, the impurity which is present mainly in the surface area is removed by partially melting the crystal. As described in the above, in the purification by crystallization, both of cold energy for crystallizing (meth)acrylic acid and heat energy for melting the obtained crystal are required.

A refrigerator is employed for generating both of cold energy and heat energy. As a refrigerator, there are various types such as an absorption type refrigerator and a compression type refrigerator.

In an absorption type refrigerator, a liquid refrigerant for a refrigerator is evaporated to obtain vaporization heat and a cooling medium is cooled using the vaporization heat. The cooled cooling medium is provided to the outside.
The vaporized refrigerant for a refrigerator is absorbed in an absorbing liquid and then a refrigerant gas is separated from the solution in a rectification column or the like. The obtained refrigerant gas for a refrigerator is condensed to be devolatilized again, and a heating medium is heated by the condensation heat generated at the time and the heated heating medium is supplied to the outside. In a compression type refrigerator, a refrigerant gas for a refrigerator is directly compressed to obtain condensation heat without using an absorption liquid for absorbing or regenerating the refrigerant gas for a refrigerator. In any cases, a refrigerator can efficiently supply both of a cooling medium and a heating medium by repeating vaporization and devolatilization of a refrigerant for a refrigerator.

As described above, a refrigerator which can generate cold energy and heat energy is generally used in the crystallization purification of (meth)acrylic acid, since both of cold energy and heat energy are needed. Therefore, a method for efficiently producing (meth)acrylic acid using a refrigerator has been developed.

For example, Patent Document 1 discloses a method for producing an organic acid such as (meth)acrylic acid, wherein reaction heat and combustion heat of waste are recovered to be used as a heat source for an absorption type refrigerator. According to the method, the energy which has been discarded can be utilized effectively and thus it is made possible to save the product cost.

PRIOR ART

Patent Document

Patent Document 1: JP2007-277182A

DISCLOSURE OF THE INVENTION

Problems to be Solved by the Invention

As described above, conventionally, a refrigerator has been commonly used in the purification by crystallization of (meth)acrylic acid. However, the operation condition has not been sufficiently investigated and conventional methods have been not satisfactory in some cases.

As mentioned above, both of cold energy and heat energy are needed in the purification by crystallization of (meth)acrylic acid for carrying out crystallization, melting and the like. Therefore, for example, when a crystallization step and a melting step are carried out in parallel, a refrigerator can be operated in an almost steady state, since both of a cooling medium and a heating medium obtained from a refrigerator are utilized and both loads for cooling and heating are applied to the refrigerator.

However, in the initial period of the purification by crystallization, only a crystallization step is carried out. In such a case, only a cooling load is applied to a refrigerator. Specifically, in the initial period of crystallization purification, a cooling medium supplied from a refrigerator is used for cooling a crude (meth)acrylic acid solution and warmed in a crystallizer and thereafter returned to the refrigerator. On the other hand, a heating medium is returned to a refrigerator without giving heat in a crystallizer. As a result, a refrigerator cannot sufficiently exhibit the cooling capability thereof and consequently, the temperature of a cooling medium to be supplied becomes higher than the set temperature, since the refrigerator is required to carry out cooling but is not required to carry out heating. Finally, since the temperature of a cooling medium supplied to a crystallizer becomes high, a crude (meth)acrylic acid solution cannot be sufficiently cooled and crystallization cannot be stably carried out.

Under the above-described circumstance, the objective of the present invention is to provide a method for efficiently producing (meth)acrylic acid by crystallization using a plurality of crystallizers to purify (meth)acrylic acid and a refrigerator for supplying both of a cooling medium and a heating medium, while the refrigerator is stably operated for supplying media having a proper temperature and the temperature of the crystallizers is maintained.

Means for Solving the Problems

The present inventors engaged in diligent research to solve the above-described problem. As a result, the present inventors found the following solution means and completed the present invention. Specifically, the temperature of a heating medium returned to a refrigerator is previously decreased to be lower than the set temperature before starting the crystallization of (meth)acrylic acid. In such a condition, a cooling medium having a proper set temperature can be stably supplied even in the crystallization initial period in which only a cooling medium is required, and thus, (meth)acrylic acid can be produced efficiently.

The method for producing (meth)acrylic acid according to the present invention is characterized in
comprising the steps of at least crystallizing (meth)acrylic acid and melting the (meth)acrylic acid crystal obtained in the crystallization step;
wherein
two or more crystallizers are employed;
when both of the crystallization step and the melting step are concurrently carried out in separate crystallizers, a cooling medium is supplied to a crystallizer for carrying out the crystallization step to crystallize (meth)acrylic acid and a heating medium is supplied to other crystallizer for carrying out the melting step to melt the (meth)acrylic acid crystal from a refrigerator; and
when only the crystallization step is carried out before the melting step is carried out, a temperature of a heating medium to be returned to the refrigerator is previously decreased to be lower than a set temperature for the melting step before only the crystallization step is carried out.

In the present invention method, when only the melting step is carried out after completion of the crystallization step, it is preferred that a cooling load on the refrigerator is reduced in comparison with a cooling load for the crystallization step. When the crystallization step is finished and only the melting step is carried out, only a heating medium is utilized and a cooling medium is directly returned to the refrigerator without giving cold energy in the crystallizer. Therefore, if a cooling load on the refrigerator is left as the cooling load at the time the cold energy of the cooling medium is used in the crystallizer, the cooling medium which has a relatively high temperature and which is stored in a buffer tank is consumed, and thus, the temperature of the cooling medium to be returned to the refrigerator may become low. As a result, no cooling load is applied to the refrigerator and stable supply of a heating medium may become impossible. In the present invention, the cooling medium which has a relatively high temperature and which is stored in a buffer tank is gradually used and the minimum cooling load is applied to the refrigerator for a relatively long time by decreasing the cooling load of the refrigerator. Under such a condition, the refrigerator can more certainly supply a heating medium stably.

In the present invention method, before only the crystallization step is carried out at the start of crystallization purification, it is preferred that a temperature of a heating medium to be returned to the refrigerator is previously lowered in the range of not less than 5° C. and not more than 35° C. lower than the set temperature for the melting step. If the temperature of a heating medium to be returned to the refrigerator is adjusted to lower than the set temperature for the melting step by not less than 5° C., a sufficient heating load is applied to the refrigerator due to the difference from the set temperature of the heating medium for the melting step, and it becomes possible that the refrigerator stably supplies a cooling medium even if only the crystallization step is carried out and only a cooling medium is used in the crystallizer. On the other hand, if the temperature of a heating medium to be returned to the refrigerator is lower than the set temperature by more than 35° C., excess time and energy are consumed in the preliminarily operation; and therefore, the temperature difference is preferably not more than 35° C.

In the present invention method, when only the melting step is carried out after completion of the crystallization step, it is preferred that a cooling load on the refrigerator is set at the range of not less than 10% and not more than 40% of a rated capacity of the refrigerator. If a set temperature of a cooling medium to be returned to the refrigerator is lowered below a set temperature for the crystallization step so that a cooling load on the refrigerator is set to be not less than 10% of a rated capacity of the refrigerator, it becomes possible that the refrigerator can stably supply a heating medium since the refrigerator has a sufficient cooling load even in the case where only the melting step is carried and only a heating medium is used in the crystallizer. On the other hand, if a cooling load exceeds 40% of a rated capacity of the refrigerator, since a cooling medium is not used in the crystallizer and a cooling load cannot help but depend on the heat storage capacity of a buffer tank. As a result, the heat storage capacity may not become sufficient. Therefore, a cooling load is preferably not more than 40% of a rated capacity of the refrigerator.

The method for producing a hydrophilic resin and the method for producing a water-absorbing resin according to the present invention are characterized in comprising the step of polymerizing a monomer component containing (meth) acrylic acid produced by the above-described method according to the present invention.

MODE FOR CARRYING OUT THE INVENTION

The method for producing (meth)acrylic acid according to the present invention is characterized in
comprising the steps of at least crystallizing (meth)acrylic acid and melting the (meth)acrylic acid crystal obtained in the crystallization step;
wherein
two or more crystallizers are employed;
when both of the crystallization step and the melting step are concurrently carried out in separate crystallizers, a cooling medium is supplied to a crystallizer for carrying out the crystallization step to crystallize (meth)acrylic acid and a heating medium is supplied to other crystallizer for carrying out the melting step to melt the (meth)acrylic acid crystal from a refrigerator; and
when only the crystallization step is carried out before the melting step is carried out, a temperature of a heating medium to be returned to the refrigerator is previously decreased to be lower than a set temperature for the melting step before only the crystallization step is carried out.

The present invention method comprises at least a crystallization step for obtaining a (meth)acrylic acid crystal by crystallization from a crude (meth)acrylic acid solution and a melting step for melting the (meth)acrylic acid crystal.

A crude (meth)acrylic acid solution is not particular limited as long as it contains impurity in addition to (meth) acrylic) acrylic acid as the target compound. For example, a crude (meth)acrylic acid solution may be obtained by carrying out a gas-phase catalytic oxidation reaction to obtain a gas containing (meth)acrylic acid and contacting the gas with a collecting liquid or condensating the gas. The crude (meth) acrylic acid solution obtained by contacting a gas containing (meth)acrylic acid with a collecting liquid or condensing the gas includes by-product impurity such as water, acetic acid, propionic acid, maleic acid, acetone, acrolein, furfural and formaldehyde in addition to (meth)acrylic acid and a unreacted raw material.

In order to obtain higher purity (meth)acrylic acid, a crystallization purification may be repeated two or more times. Specifically, once (meth)acrylic acid is purified by crystallization, and the purified (meth)acrylic acid may be melted to be supplied to a crystallizer in place of a crude (meth)acrylic acid solution for crystallization.

In the present invention method, (meth)acrylic acid is crystallized to be purified by using a crystallizer, and the type of a crystallizer is not particularly limited. For example, a crystallizer having a heat transfer face and capable of crystallizing (meth)acrylic acid by heat exchange on the heat transfer face can be employed. In such a case, the inside of a crystallizer is preferably divided by a heat transfer face into apart (location of medium) to which a cooling medium or a heating medium is supplied and a part (location of crystal) in which a (meth) acrylic acid solution and/or a (meth)acrylic acid crystal is present.

In the case that a crystallizer has a heat transfer face, (meth)acrylic acid is crystallized from a (meth)acrylic acid solution in the crystallization step and the crystallized (meth)) acrylic acid is melted in the melting step by heat exchange on the heat transfer face. In more detail, in the crystallization step, a cooling medium is supplied to a crystallizer, and at the same time, a (meth)acrylic acid solution is supplied to the crystallizer so that the crude (meth)acrylic acid solution is cooled by the cooling medium through a heat transfer face to crystallize (meth)acrylic acid. In the melting step, a heating medium is supplied to a crystallizer and the crystallized (meth)acrylic acid is heated by the heating medium through a heat transfer face to be melted. Alternatively, a (meth)acrylic acid crystal may be melted using a (meth)acrylic acid solution heated by a heating medium.

As a crystallizer having a heat transfer face, an apparatus to be used generally as a heat exchanger can be employed, and it is particularly preferable to employ an apparatus to be used as a heat exchanger in which heat exchange is carried out between liquids. Such an apparatus to be used is exemplified by a plate type heat exchanger in which one plate is arranged or plural plates are layered at intervals and in which a location of medium and a location of a crystal are alternately arranged with sandwiching the plate; a multi-tubular type heat exchanger or a shell and tube type heat exchanger in which plural tubes are arranged in a container to carry out heat exchange between the inside and the outside of the tubes; a double tube type heat exchanger having an outer tube and an inner tube arranged in the outer tube to carry out heat exchange between the inside and the outside of the inner tube; a coil type heat exchanger having a single tube arranged in a coil-like state in a container to carry out heat exchange between the inside and the outside of the tube; and a spiral type heat exchanger in which two spirally wound channels are formed by spirally rolled two heat transfer plates on a center tube divided in two in a cross section. There is no particular limitation of a cross section shape of a tube to be employed for a multi-tubular heat exchanger, a double tube type heat exchanger, a coil type heat exchanger, and a spiral type heat exchanger.

The melting point of acrylic acid is 13.5° C., and the melting point of methacrylic acid is 16° C. In the crystallization step, since a crude (meth)acrylic acid solution contains impurity, the solidification point of (meth)acrylic acid is lower than the melting points; however, (meth)acrylic acid is crystallized by sufficiently cooling the solution. Such a cooling procedure may be preformed in two or more stages. Specifically, it can be said that the purity of a crystal is higher when the crystal is obtained at a relatively high temperature over a long time than the case that a crystal is obtained at a relatively low temperature in a short time. In addition, it is also known that if the crystal purity in the initial period of crystallization is high, the purity of a crystal grown thereafter can be increased. Therefore, it is preferable to obtain a crystal with a high purity by setting the cooling temperature of a crude (meth)acrylic acid solution in the initial period of crystallization to be relatively high and thereafter to sufficiently grow the crystal by lowering the cooling temperature.

After the crystallization step, a (meth)acrylic acid crystal and a solution are separated. The means for separation is not particularly limited, and filtration, centrifugation or the like may be employed. Alternatively, in the case of using a falling liquid film crystallizer or the like, a solution is spontaneously discharged.

(Meth)acrylic acid obtained in the crystallization step is subjected to the melting step. The melting step is carried out for liquefying (meth)acrylic acid to make transportation to the next step easy and to get the crystal out of a crystallizer. The melting step includes a sweating procedure to increase the purity.

In the crystallization step, the amount of impurity present in the solution is increased relatively with the progression of the crystallization of (meth)acrylic acid; therefore, impurity may possibly adhere to the surface of a (meth)acrylic acid crystal in some cases. Accordingly, the surface of a (meth) acrylic acid crystal is partially melted and the melted portion is removed to increase the purity of the crystal. Such a partial melting treatment is called as a sweating procedure.

The melting step may be carried out by heating a (meth) acrylic acid crystal to the melting point or higher. The melting step may be carried out in two or more stages using a plurality of heating media having different temperatures similarly to the crystallization step.

In the present invention method, two or more crystallizers and a refrigerator which can supply both of a cooling medium and a heating medium are employed.

The type of a refrigerator is not particularly limited as long as both of a cooling medium and a heating medium can be supplied by the refrigerator, and is exemplified by an absorption type refrigerator such as an ammonia-absorption type and a water-lithium bromide type, a compression type refrigerator and an adsorption type refrigerator.

Figure 1:
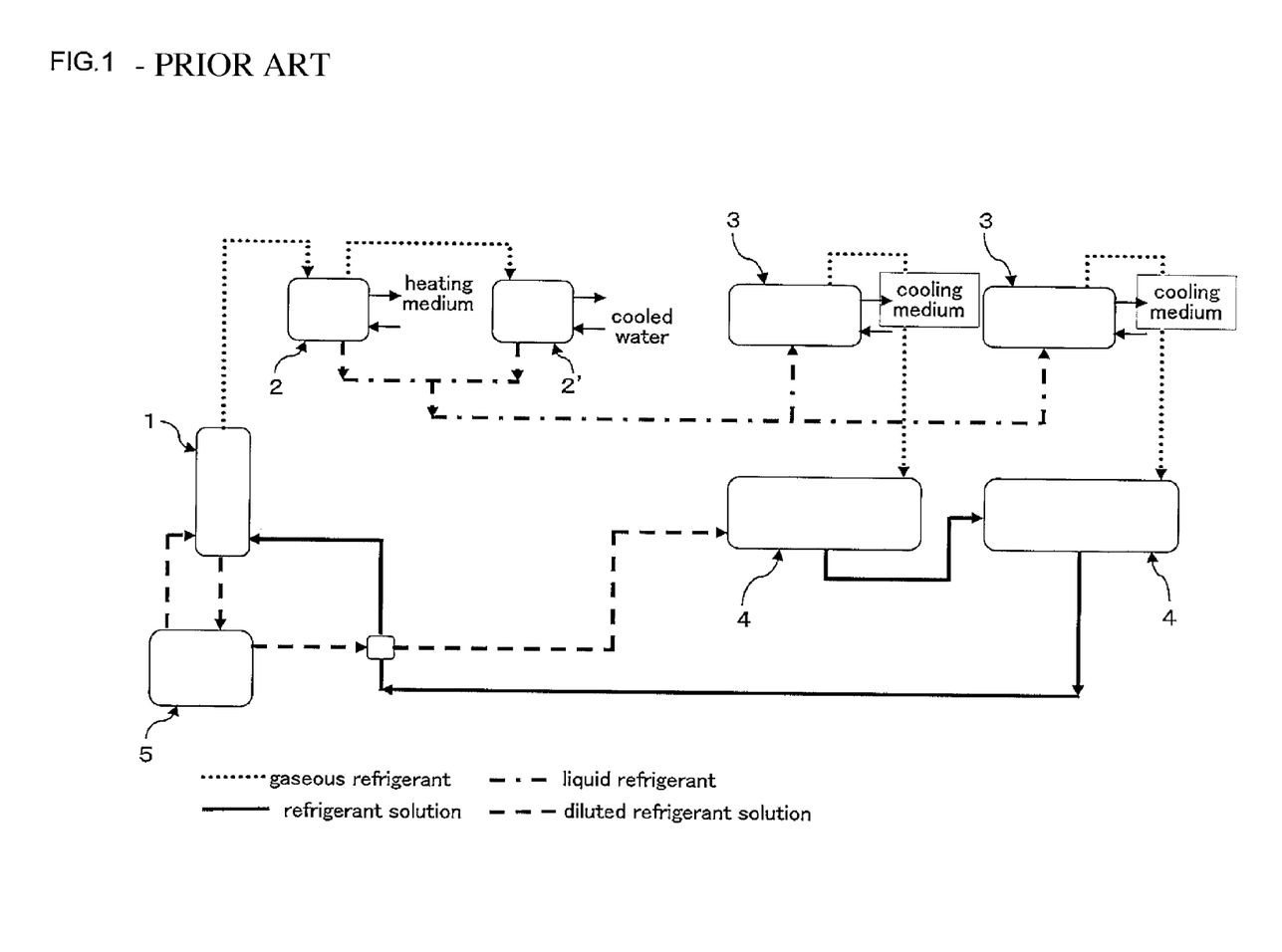
FIG. 1 is a diagrammatic illustration of one example of a refrigerator to be used in the present invention method. In the figure, "1" is a rectifier; "2" is a condenser; "3" is an evaporator; "4" is an absorption device; and "5" is a generator.

FIG. 1 shows one example of an absorption type refrigerator which can be used in the present invention. The refrigerator shown in FIG. 1 can supply one kind of a heating medium and two kinds of cooling media; but needless to say, a refrigerator to be used in the present invention is not limited to this type.

In the refrigerator shown in FIG. 1, an aqueous refrigerant solution for a refrigerator is separated into a refrigerant gas for a refrigerator and a diluted refrigerant solution for a refrigerator in a rectifier 1. A refrigerant for a refrigerator is not particularly limited as long as it has a low boiling point and is relatively easy to be vaporized and water-soluble. For example, ammonia and methanol are used as a refrigerant. The refrigerant for a refrigerator vaporized in a rectifier is cooled to be devolatilized in a condenser 2. It becomes possible that a heating medium is heated to a set temperature by the condensation heat generated at that time. The heating temperature at that time can be adjusted by supplying a portion of the refrigerant gas for a refrigerator to another condenser 2'. A portion of the remaining refrigerant for a refrigerator is condensed using cooling water. Hereinafter, a refrigerant for a refrigerator is simply referred to as "refrigerant".

A liquefied refrigerant is vaporized by an evaporator 3. A cooling medium is cooled to a set temperature by the vaporization heat generated at that time. The cooling extent can be adjusted in accordance with the distribution amount of a refrigerant to be supplied to two evaporators, the temperature of the liquefied refrigerant, the pressure at the time of evaporation and the like.

The refrigerant vaporized by the evaporator 3 is absorbed in a diluting solution (an absorbing solution) for a refrigerant in an absorption device 4. The thus obtained aqueous refrigerant solution is transported to a rectifier, and separated into a refrigerant gas and a diluted refrigerant solution.

The kind of a medium to be cooled or heated by a refrigerator of the present invention is not particularly limited, and is exemplified by an aqueous ethylene glycol solution, an aqueous glycerin solution and an aqueous methanol solution.

An absorption type refrigerator is exemplified for the above-mentioned explanation; however, a compression type refrigerator and an adsorption type refrigerator which can supply both of a cooling medium and a heating medium may be employed. For example, a compression type refrigerator has a smaller waste heat quantity as compared with an adsorption type refrigerator with the same capacity, and is therefore advantageous in miniaturizing a cooling apparatus. An adsorption type refrigerator is advantageous in that maintenance therefor is easy and the operation can be carried out safely.

As described above, by using a refrigerator which can supply both of a cooling medium and a heating medium, cooling of a cooling medium and heating of a heating medium can be carried out by heat exchange through a refrigerant. In the present invention method, since two or more crystallizers are used, the crystallization step and the melting step can be carried out in parallel, and both of a cooling medium and a heating medium supplied from a refrigerator can be utilized in steady operation, so that (meth)acrylic acid can be efficiently produced.

As described above, in the present invention method, (meth)acrylic acid can be efficiently produced by using two or more crystallizers and a refrigerator which can supply both of a cooling medium and a heating medium. In particular, the production efficiency is high in the case that the crystallization step and the melting step are carried out in parallel.

However, since only the crystallization step is carried out in an initial period of the crystallization purification, only a cooling medium is used in a crystallizer even if both of a cooling medium and a heating medium are supplied from a refrigerator. In other words, a cooling medium is heated instead of cooling a crude (meth)) acrylic acid solution in a crystallizer; on the other hand, a heating medium is returned as it is to a refrigerator without being utilized. As a result, only a cooling load for cooling a cooling medium heated in a crystallizer is generated in the refrigerator. As shown in FIG. 1, a cooling medium is cooled by vaporization heat generated at the time of gasifying a liquid-state refrigerant. When there is no heating load, the heat generated at the time of re-liquefying a refrigerant gas has to be absorbed only with cooling water. Consequently, a cooling load of a cooling medium exceeds the capacity of a refrigerator and it sometimes becomes impossible to cool a cooling medium to the set temperature; as a result, sufficient crystallization of (meth) acrylic acid may possibly become impossible in some cases.

Therefore, in the present invention method, when only the crystallization step is carried out before the melding step is carried out, a temperature of a heating medium to be returned to the refrigerator is previously decreased to be lower than a set temperature for the melting step before only the crystallization step is carried out.

Hereinafter, the conditions for practicing the present invention are explained with reference to specific example; however, the present invention is not limited to the specific example.

Figure 2:
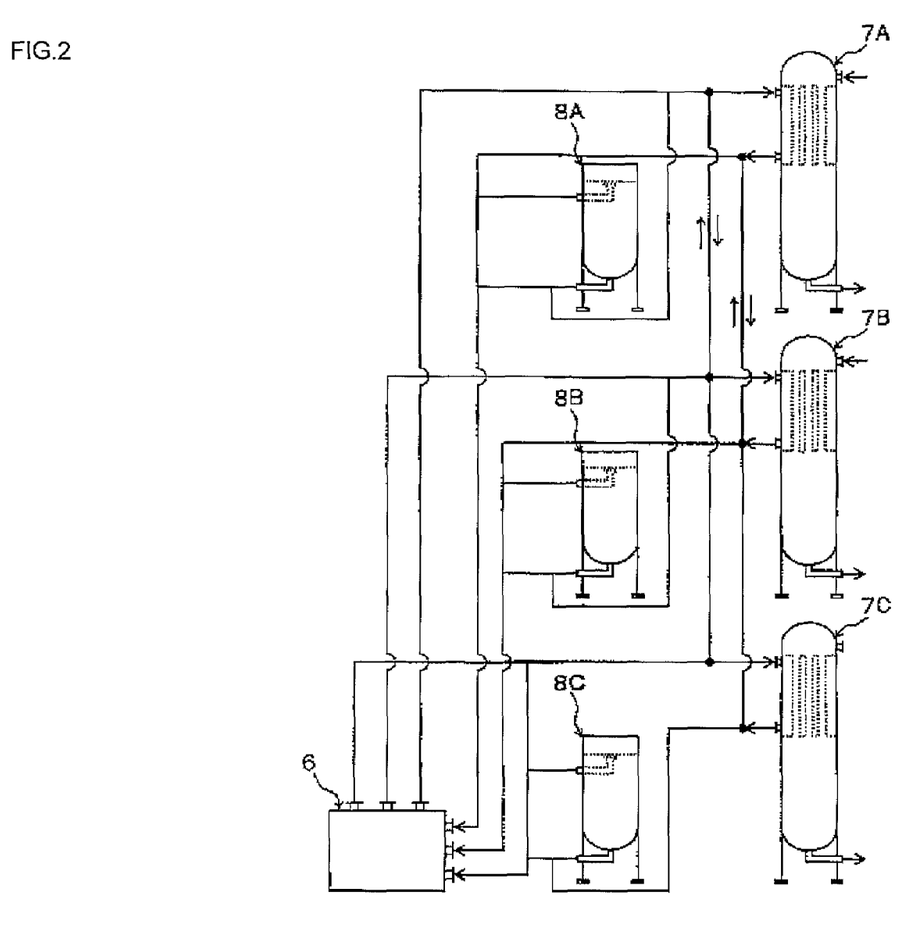
FIG. 2 is a diagrammatic illustration of one example of a system for crystallization purification of (meth)acrylic acid for carrying out the present invention method. In the figure, "6" is a refrigerator; "7A to 7C" are crystallizers; and "8A to 8C" are buffer tanks.

FIG. 2 shows a diagrammatic illustration of a system for carrying out the present invention method. In the system shown in FIG. 2, three crystallizers are employed; however, the number of crystallizers may be actually 2, or may be not less than 4.

Each one kind of cooling medium and heating medium may be used, or not less than two kinds of cooling media or heating media with different temperatures may be used. For example, a crystal with higher purity may be obtained at a relatively high temperature over a long time and then a crude solution may be cooled at a relatively low temperature to sufficiently promote crystallization.

For example, in the case of purifying acrylic acid, in order to cool a heat transfer face of a crystallizer to the melting point or lower, the set temperature of a cooling medium at a relatively high temperature may be not less than about $-10°$ C. and not more than about $10°$ C., and the set temperature of a cooling medium at a relatively low temperature may be not less than about $-30°$ C. and not more than about $-10°$ C.

In the case of acrylic acid, the set temperature of a heating medium to be supplied to a crystallizer for the melting step may be not less than about $+20°$ C. and not more than about $+40°$ C.

Needless to say, the above-described respective set temperatures are mere examples and actual set temperatures can be determined properly in accordance with the surface area of a heat transfer face of a crystallizer, the supply amount of a crude (meth)acrylic acid solution to a crystallizer, the supply amount of a medium, and the like.

In general, before crystallization purification of (meth) acrylic acid, media are supplied to each crystallizer to stabilize the temperature. For example, in the system shown in FIG. 2, before purification by crystallization, a cooling medium having a relatively high temperature may be supplied to a crystallizer 7A and a cooling medium having a relatively low temperature may be supplied to a crystallizer 7B for cooling respectively, and a heating medium may be supplied to a crystallizer 7C. However, in the initial period of crystallization purification, no medium is supplied to a crystallizer in which the crystallization step is not carried out, and a medium supplied from a refrigerator may be returned to the refrigerator via buffer tanks 8A to 8C.

In the present invention method, before the purification by crystallization, the temperature of a heating medium to be returned to a refrigerator is previously lowered than the set temperature for the melting step. In other words, a refrigerator is operated so that the temperature of a heating medium supplied from the refrigerator is set to be lower than the set temperature of a heating medium to be used in the melting step, and a sufficient amount of a heating medium having a temperature lower than the temperature for the melting step is made to exist in a buffer tank.

As a result, before the crystallization purification of (meth) acrylic acid, a cooling medium is stored in a buffer tank at a temperature almost the same as the set temperature for the crystallization step; on the other hand, a heating medium is stored in a buffer tank at a temperature lower than the temperature for the melting step. At that time, a cooling load larger than a heating load may be possibly applied to a refrigerator and therefore the cooling capacity of the refrigerator may considerably decrease. However, since there is no problem even if the temperature of the medium supplied from the refrigerator is disturbed before the purification by crystallization, the refrigerator may be operated until a cooling medium and a heating medium gradually come to have the predetermined temperatures.

The temperature of a heating medium at the time of the operation before crystallization purification is decreased to be lower than the set temperature of the melting step in accordance with the cooling load generated in a refrigerator for cooling a cooling medium enough to crystallize (meth)acrylic acid from a crude solution in the crystallization step. Specifically, the temperature may be properly determined depending on the supply amount of a crude (meth)acrylic acid solution, the set temperature and supply amount of a cooling medium, the set temperature of a heating medium in the melting step, the supply amount of a heating medium, and the like; and it is preferable to set the temperature to be lower than the set temperature of the melting step by not less than 5° C. and by not more than 35° C. When the temperature of a heating medium to be returned to a refrigerator is set to be lower than a set temperature of the melting step by 5° C. or more, the cooling load generated for cooling a cooling medium in a refrigerator can be sufficiently balanced out even in the case that only the crystallization step is carried out in the initial period of crystallization purification. On the other hand, when the temperature of a heating medium to be returned to a refrigerator is set to be lower than the set temperature for the melting step by more than 35° C., excess time and energy are consumed in the preliminarily operation and therefore the temperature difference is preferably not more than 35° C.

Due to the above-described preliminarily operation, the temperature of a cooling medium returned to a crystallizer is stabilized to be the set temperature of the crystallization step, and a heating medium having a temperature lower than the set temperature for the melting step is sufficiently stored in a buffer tank for a heating medium. Next, the temperature of a heating medium to be supplied to a crystallizer from a refrigerator is stabilized at the set temperature for the melting step. Thereafter, in order to start the purification by crystallization, a crude (meth)acrylic acid solution is supplied to a crystallizer. In the system shown in FIG. 2, first, a crude (meth) acrylic acid solution is supplied to the crystallizer 7A to which a cooling medium having a relatively high temperature is supplied.

In the system shown in FIG. 2, a cooling medium having a relatively high temperature is supplied to the crystallizer 7A for cooling to crystallize (meth)acrylic acid from a crude solution. The time to be taken for the crystallization of the first stage is determined depending on the concentration of a crude (meth)acrylic acid solution, a cooling temperature, and the like, and may be generally not less than about 5 minutes and not more than about 90 minutes. However, it is preferable to properly shorten the time with observing the crystallization state from the viewpoint of improvement of the production efficiency.

When only the crystallization step is carried out in the initial period of the crystallization purification, only a cooling load is generated but a heating load is not generated in a refrigerator. Therefore, in order to cool the cooling medium heated for cooling a crude (meth)acrylic acid in a crystallizer, a liquid-state refrigerant has to be vaporized in a refrigerator to take heat from a cooling medium. In order to continuously obtain a condensation heat, a refrigerant gas has to be condensed again to be devolatilized.

In the case that the crystallization step is carried out in two stages and only the crystallization is carried out in the first stage by using a cooling medium having a relatively high temperature, it may be possible to remove the condensation heat generated by condensing a refrigerant gas only with cooling water as described above (see FIG. 1). However, in the case that it is impossible to remove the condensation heat only with cooling water, a refrigerator may not cool a cooling medium to the set temperature and crystallization of (meth) acrylic acid may not proceed sufficiently. In such a case, a heating medium having a relatively low temperature which is previously stored in a buffer tank is returned to the refrigerator. As a result, a heat load corresponding to the difference between the temperature of a heating medium to be returned to the refrigerator and the temperature for the melting step is applied to the refrigerator, and therefore the refrigerator can be stably operated and a cooling medium of the set temperature can be supplied stably.

In more detail, in the preliminarily operation, the temperature of a heating medium is set to be lower than the set temperature for the melting step so that a buffer tank for a heating medium can be filled with a heating medium having a temperature lower than the set temperature for the melting step. A heating medium is not utilized in a crystallizer and the temperature thereof is scarcely changed even if the heating medium passes through the crystallizer; however, since the buffer tank is filled with a heating medium having a lower temperature, it becomes possible to return a heating medium having a temperature in the preliminarily operation to the refrigerator by supplying the heating medium returned from the crystallizer to an upper part of the buffer tank and draining the heating medium from a lower part thereof. As a result, since a heating load is applied to a refrigerator due to the difference between the set temperature in the preliminarily operation and the set temperature for the melting step, even if only a cooling medium is utilized in a crystallizer, both of a cooling load and a heating load are applied to a refrigerator and thus the refrigerator can stably supply a cooling medium of the set temperature.

Hereinafter, a buffer tank to be used in the present invention method is described.

A buffer tank to be used in the present invention method has two apertures, specifically, an upper aperture and a lower aperture; and has a vertically long shape and a heat-insulating structure to the outside so that the buffer tank is able to store heat.

To keep temperature gradient of a medium in a buffer tank, the buffer tank is required to have a vertically long structure and stirring or convection of the inside medium is prevented from occurring. As a result, for example, when a medium having a higher temperature than that of a medium present in a buffer tank is supplied to the upper part of the buffer tank and a medium to be returned to a refrigerator is drained from the lower part, the temperature gradient of a medium in the buffer tank can be maintained.

The shape of a buffer tank is not particularly limited as long as the buffer tank has a vertically long structure, and it is preferable that a buffer tank has an approximately column body such as a cylindrical column and a rectangular column. The length of the straight trunk part of a buffer tank is preferably 1 or more times as long as the maximum length of a cross section of the buffer tank. When the ratio is 1 or more times, the temperature gradient of the medium present in the inside of a buffer tank can be sufficiently maintained. In the present invention, the maximum length of the cross section of a buffer tank means, for example, the diameter of the circle of the bottom face when the buffer tank has a cylindrical column shape. When the buffer tank has a rectangular column shape, the maximum length of a cross section of the buffer tank means the diagonal length of the rectangular shape of the bottom face. When the buffer tank has a rectangular column shape portion excluding a lower part and a cone shape tapered downward in the lower part, the maximum length of a cross section of the buffer tank means the maximum length of a cross section of the column part. When the buffer tank has a shape expanded at the middle area in the height direction, the maximum length of a cross section of the buffer tank means the maximum length of a cross section of the most expanded portion at the middle part.

In order to maintain a temperature gradient of a medium in a buffer tank, it is necessary to make convection of the medium difficult to occur. For example, a pipe for supplying a medium into a buffer tank is expanded to the center part in a cross section of the buffer tank, and the opening of the pipe for supplying a medium is turned upward in an upper part. In addition, a rectifier may be installed at the opening part of the pipe for suppressing ejection of a medium as much as possible.

As described above, a temperature gradient can be maintained in a buffer tank. Consequently, even if a heating medium of the set temperature for the melting step is supplied to a buffer tank without giving heat, it becomes possible to apply a heating load to a refrigerator by supplying the heating medium to the upper part of the buffer tank and draining a heating medium having a relatively low temperature stored in the buffer tank in the preliminary step to supply the drained heating medium to the refrigerator. As a result, even if only a cooling medium is used in a crystallizer in the initial period of the crystallization purification, both of a cooling load and a heating load are applied to a refrigerator and thus the refrigerator can stably supply a cooling medium of the set temperature.

In the system shown in FIG. 2, at the time of starting crystallization purification, the crystallization step is carried out only in the crystallizer 7A. Only a cooling load is therefore applied to the refrigerator. However, when such a cooling load can be removed, it is not needed to use the heating medium having a relatively low temperature previously stored in a buffer tank for a heating medium as described above. Such a case is exemplified by a case that the condensation heat which is generated at the time of re-liquefying a vaporized refrigerant to generate a cold energy for cooling a cooling medium can be removed with cooling water in the refrigerator schematically shown in FIG. 1.

However, when the crystallization step is continued in the system as shown in FIG. 2, a cooling load generated in the refrigerator may not be removed with cooling water only. Specifically, after completion of the crystallization in the first stage in the crystallizer 7A, a valve in a medium line is turned to supply a cooling medium having a relatively low temperature to the crystallizer 7A and supply a cooling medium having a relatively high temperature to the crystallizer 7B. After the temperature of the crystallizer 7B is stabilized, a crude (meth)acrylic acid solution is supplied to the crystallizer 7B. As a result, both of two kinds of cooling media supplied from the refrigerator are used in crystallizers to be heated, and a cooling load for cooling the media again to the set temperature is applied to the refrigerator; therefore, stable operation of the refrigerator may become impossible using only cooling water without a heating load.

In such a case, a heating medium having a relatively low temperature previously stored in a buffer tank for heating is utilized to lower the temperature of a heating medium to be returned to the refrigerator, and thus a heating load is applied to the refrigerator. As a result, the refrigerator can be stably operated and a cooling medium can be stably supplied even when only the crystallization step is carried out.

In the case that two-stage crystallization is carried out, the crystallization in the second stage may be carried out by supplying a cooling medium having a lower temperature to a crystallizer to further cool a heat transfer face. Similarly to the crystallization of the first stage, the time required for the crystallization in the second stage depends on the concentration of a crude (meth)acrylic acid solution, a cooling temperature and the like, and is generally not less than 5 minutes and not more than 90 minutes. It is preferable to properly shorten the time with observing the crystallization state from the viewpoint of improvement of the production efficiency.

In the system shown in FIG. 2, after completion of the second stage crystallization in the crystallizer 7A and the first stage crystallization in the crystallizer 7B, a heating medium is supplied to the crystallizer 7A, a cooling medium having a relatively low temperature is supplied to the crystallizer 7B and a cooling medium having a relatively low temperature is supplied to the crystallizer 7C. Thus, the melting step, specifically the sweating procedure or the melting procedure, is carried out in the crystallizer 7A; the second stage crystallization is carried out in the crystallizer 7B; and the first stage crystallization is carried out in the crystallizer 7C. Since both of a heating medium and a cooling medium are used in crystallizers and both of a cooling load and a heating load are applied to the refrigerator in this case, it becomes possible to stably operate the refrigerator and to stably supply both of a cooling medium and a heating medium.

The sweating procedure in the melting step is carried out for partially dissolving and separating only the surface of a (meth)acrylic acid crystal to remove impurity adhered to the surface and to remove impurity present in a larger amount in the crystal surface area.

It is not needed to particularly strictly determine the time of the melting procedure, and heating may be continued until a (meth)acrylic acid crystal is sufficiently melted. Accordingly, the time of the melting step including the sweating procedure and the melting procedure can be adjusted depending on the crystallization step carried out in another crystallizer.

Thereafter, both of a heating medium and a cooling medium are constantly used by repeating the crystallization step and the melting step in each crystallizer. As a result, a refrigerator can be stably operated and (meth)acrylic acid can be stably crystallized to be purified.

The utilization degree of a medium is changed even during a single step. For example, when crystallization or the like is not completed in other crystallizer, it is sometimes necessary to wait in certain crystallizer between a step and the next step. During such a waiting, energy of a medium is hardly used. In such a case, it is preferable that the temperature change of a medium to be returned to a refrigerator is suppressed and a load on the refrigerator is kept to be constant by utilizing a buffer tank.

In order to suppress the temperature change of a medium to be returned to a refrigerator, a buffer tank is used. For example, when a cooling medium is highly heated in a crystallizer, the cooling medium after passing through the crystallizer may be supplied to an upper part of a buffer tank and a cooling medium having a relatively low temperature may be drained from a lower part to be returned to a refrigerator. Alternatively, a part of a cooling medium may not be supplied to a crystallizer and mixed with a cooling medium drained from a lower part of the buffer tank. Contrarily, when the temperature of a cooling medium after passing through a crystallizer is lowered more than the initial temperature, the temperature may be adjusted by supplying a part of the cooling medium to a buffer tank and draining the corresponding amount of a cooling medium having a relatively high temperature from an upper part of the buffer tank to be mixed with the remaining cooling medium.

As described above, when the crystallization step and the melting step are carried out in parallel by using two or more crystallizers, both of a cooling medium and a heating medium are used so that a refrigerator can be stably operated within the rated capacity. On the other hand, a problem may arise not only at the time of starting the crystallization purification but also at the time of finishing the crystallization purification.

For example, in the system shown in FIG. 2, after the melting step is carried out in the crystallizer 7A, the second stage crystallization step is carried out in the crystallizer 7B and the first stage crystallization step is carried out in the crystallizer 7C, when the melting step is carried out in the crystallizer 7B and the second stage crystallization step is carried out in the crystallizer 7C, a heating medium is supplied to the crystallizer 7B and a cooling medium having a relatively low temperature is supplied to the crystallizer 7C and a cooling medium having a relatively high temperature is supplied to the crystallizer 7A. Alternatively, a cooling medium having a relatively high temperature is directly returned to a refrigerator via a bypass without being supplied to the crystallizer. In such a case, a heating load becomes high in a refrigerator as compared with a cooling load; however, since cold energy of a cooling medium is not used, the refrigerator may be operated within the rated capacity.

However, after the melting step in the crystallizer 7B is completed, only a heating medium is used in a crystallizer and cooling media are not used since only the melting step is carried out in the crystallizer 7C. As a result, a heating load excessively increases in relation to a cooling load in the refrigeration, and a heating medium may not be heated to the set temperature in some cases.

In the melting step, a purified (meth)acrylic acid is merely melted, and the quality of (meth)acrylic acid is scarcely affected adversely unless heating is excessively carried out. Therefore, it is conceivable to carry out melting over a long time even if a heating medium can not be heated to the set temperature. However, the temperature of a heating medium has to be kept at the set temperature in the sweating procedure, since the purity of (meth)acrylic acid may possibly be lowered if the heating temperature is disturbed in the sweating procedure. In addition, although the quality of (meth) acrylic acid is basically not affected depending on a temperature in the melting procedure, the supply of a heating medium having the set temperature has to be similarly maintained since the production efficiency is lowered if the operation takes a long time.

Accordingly, in the present invention method, it is preferable that when only the melting step is carried out after completion of the crystallization step, a cooling load on the refrigerator is reduced in comparison with a cooling load for the crystallization step. When such an operation is carried out, a cooling medium having a relatively high temperature stored in a buffer tank for a cooling medium can be gradually used and it becomes possible to continuously apply the minimum cooling load on a refrigerator over a relatively long time.

In order to lower a cooling load on a refrigerator less than a cooling load for the crystallization step, for example, the set temperature of a cooling medium to be returned to a refrigerator may be lowered less than the set temperature for the crystallization step. More specifically, a cooling medium after passing through a crystallizer may be supplied to a lower part of a buffer tank and a cooling medium having a relatively high temperature may be drained from an upper part to be returned to a refrigerator. For example, in the case that a portion of a cooling medium supplied from a refrigerator is returned directly to the refrigerator without passing through a buffer tank and the remainder is supplied to the buffer tank and a cooling medium having a relatively high temperature is drained from the buffer tank to be returned to the refrigerator in the same amount as the remainder medium supplied to the buffer tank, the temperature of a cooling medium to be returned to the refrigerator can be adjusted by adjusting the above-described amounts.

In the above-mentioned case, it is preferable to set a cooling load on a refrigerator to be not less than 10% and not more than 40% of the rated capacity of the refrigerator. When a cooling load on a refrigerator is set to be not less than 10% of the rated capacity of the refrigerator, even if only the melting step is carried out, the load on the refrigerator required for heating a heating medium can be sufficiently balanced out by a cooling load. On the other hand, if the cooling load is set to be more than 40% of the steady state, a cooling medium having a relatively high temperature present in a buffer tank for a cooling medium is shortly consumed and the temperature adjustment of a cooling medium may possibly become impossible. Therefore, it is preferable to keep the cooling load to be not more than 40% of the rated capacity of the refrigerator. In the present invention, the term "the rated capacity of a refrigerator" means the maximum capacity of the refrigerator determined for each refrigerator. There are some refrigerators which can exhibit performance equal to or higher than the rated capacity; however, the rated capacity of a refrigerator is determined as a capacity with which the refrigerator can sufficiently exhibit the performance thereof. In the present invention, the rated capacity of a refrigerator to be employed is decided on the basis of the value written in a catalog or set by a manufacturer.

(Meth)acrylic acid to be subjected to the crystallization step in the present invention is not particularly limited, and may be any one which is produced by an arbitrary method. For example, (meth)acrylic acid can be produced by carrying out the steps of dehydrating glycerin or β-methylglycerin to obtain (meth)acrolein and oxidizing the obtained (meth)acrolein. Alternatively, (meth)acrylic acid can be produced by carrying out the step of dehydrating hydroxypropionic acid or 2-methylhydroxypropionic acid. Hereinafter, hydroxypropionic acid is referred to as "HP" in some cases. The steps of dehydrating glycerin and oxidizing the obtained acrolein to obtain crude acrylic acid, and the step of dehydrating HP to obtain crude acrylic acid are described below. The steps of dehydrating glycerin and oxidizing the obtained methacrolein to obtain crude methacrylic acid, and the step of dehydrating 2-methyl-HP to obtain crude methacrylic acid can be similarly carried out except that a raw material is changed. In general, since glycerin is more economical and easier to be obtained than β-methylglycerin and also HP is more economical and easier to be obtain than 2-methyl-HP, it is preferable to carry out the steps of obtaining crude acrylic acid by dehydrating glycerin and further oxidizing the resulting product, or the step of dehydrating HP to obtain crude acrylic acid.

(1) Method for Producing Acrolein by Dehydrating Glycerin

In a method for producing acrolein, glycerin is dehydrated in the presence of a catalyst.

The above-described catalyst is exemplified by an acidic solid catalyst. Such an acidic solid catalyst may be a compound having solid acidity, and is exemplified by (a) a crystalline metallosilicate, (b) a metal oxide, (c) a clay mineral, (d) a catalyst produced by supporting a mineral acid on an inorganic carrier such as α-alumina, silica, zirconium oxide and titanium oxide; and (e) a metal salt of phosphoric acid and sulfuric acid, and a catalyst produced by supporting a metal salt of phosphoric acid or sulfuric acid on an inorganic carrier such as α-alumina, silica, zirconium oxide and titanium oxide.

The example of (a) a crystalline metallosilicate may have one or more elements selected from Al, B, Fe, Ga and the like as a T atom. The crystal structure thereof is exemplified by LTA, CHA, FER, MFI, MOR, BEA, MTW or the like. The example of (b) a metal oxide includes a simple metal oxide such as $Al_2O_3$, $TiO_2$, $ZrO_2$, $SnO_2$ and $V_2O_5$ and also a composite oxide such as $SiO_2$—$Al_2O_3$, $SiO_2$—$TiO_2$, $TiO_2$—$WO_3$ and $WO_3$—$ZrO_2$. The example of (c) a clay mineral includes bentonite, kaolin and montmorillonite. The example of (d) a catalyst produced by supporting a mineral acid on an inorganic carrier includes a catalyst produced by supporting phosphoric acid or sulfuric acid on alumina, silica or zirconia. The example of (e) a salt of phosphoric acid and sulfuric acid includes $MgSO_4$, $Al_2(SO_4)_3$, $K_2SO_4$, $AlPO_4$, $BPO_4$, $Zr_3(PO_4)_4$ and others.

Specifically, a solid acid disclosed in WO 2006/087083 and WO2006/087084 can be used; and more specifically, zirconium oxide supporting phosphoric acid, sulfuric acid or tungsten oxide can be used.

Among the above-described examples, a solid catalyst with good stability is preferable, and a crystalline metallosilicate, a metal oxide, a clay mineral and the like are preferable, since the catalyst is exposed to an oxidizing atmosphere or a reducing atmosphere at a high temperature in a dehydration reaction or a regeneration treatment. As a crystalline metallosilicate, HZSM5 containing Al as a T atom and having a MFI structure is preferable. As a metal oxide, a crystalline phosphoric acid salt compound is preferable and aluminum phosphate particularly preferable.

The acid strength of HZSM5 shows strong acidity having peaks of Hammett acidity function $H_0$ at around −9 and −16 (Kenji HASHIMOTO et al., "Catalyst", vol. 29, No. 6, p. 406-409 (1987)). It is known that the acid strength of aluminum phosphate shows a solid acidity as weak as +1.5 to +4.8 on the basis of Hammett acidity function $H_0$ although such an acid strength depends on a production method and a crystal system (Kiyoko SAKAMOTO et al., Bulletin of the Chemical Society of Japan, Vol. 9, p. 681-688 (1995)).

For example, acrolein is produced by a gas-phase dehydration reaction in which a reaction gas containing a glycerin gas is contacted with a catalyst in a reactor selected from a fixed bed reactor, a fluidized bed reactor, a moving bed reactor and the like. Additionally, the reaction for producing acrolein is not limited to a gas-phase dehydration reaction in which a reaction gas containing a glycerin gas is contacted with a catalyst, and it is also possible to use a liquid-phase dehydration reaction in which a glycerin solution is contacted with a catalyst. In the latter case, a liquid-phase dehydration reaction can be carried out by a conventionally known various method such as a method using a fixed bed combined with a distillation column, a method using a stirring bath combined with a distillation column, a method using an one-stage type stirring bath, a method using a multi-stage type stirring bath, a method using a multi-stage type distillation column, and a method combining the methods. The methods may be carried out in a batch manner or a continuous manner; however, the methods are generally carried out in a continuous manner.

Hereinafter, the method for producing acrolein by employing a gas-phase dehydration reaction excellent in industrial productivity is described as an example.

A reaction gas may be a gas containing only glycerin or may be a gas containing a gas inactive on the dehydration reaction of glycerin to adjust a glycerin concentration. Such an inert gas is exemplified by steam, a nitrogen gas, a carbon dioxide gas and air. The glycerin concentration in the reaction gas is generally not less than 0.1% by mole and not more than 100% by mole, and preferably not less than 1% by mole, and more preferably not less than 5% by mole in order to economically and efficiently produce acrolein.

The catalyst used in the present invention is a catalyst for glycerin dehydration with high acrolein selectivity so that acrolein can be obtained at a high yield even if a flow rate of the reaction gas is set to be high. The flow rate of the reaction gas on the basis of gas hourly space velocity (GHSV) per unit volume of the catalyst is generally not less than 50 $hr^{-1}$ and not more than 20000 $hr^{-1}$, preferably not more than 10000 $hr^{-1}$, and more preferably not more than 4000 $hr^{-1}$ in order to economically and efficiently produce acrolein.

The reaction temperature is generally not less than 200° C. and not more than 500° C., preferably not less than 250° C. and not more than 450° C., and more preferably not less than 300° C. and not more than 400° C.

The pressure of the reaction gas is not particularly limited as long as it is within a range in which glycerin is not condensed, and is generally not less than 0.001 MPa and not more than 1 MPa, preferably not less than 0.01 MPa and not more than 0.5 MPa, and more preferably not more than 0.3 MPa.

When the dehydration reaction of glycerin is continuously carried out, a carbonaceous substance may possibly adhere to the surface of the catalyst in some cases to deteriorate the activity of the catalyst. In particular, an acrolein selectivity may be lowered and a propionaldehyde selectivity may be increased. In such a case, the carbonaceous substance adhered to the surface of the catalyst can be removed and the activity of the catalyst can be recovered by carrying out a regeneration treatment in which the catalyst is contacted with a regeneration gas at a high temperature. Such a regeneration gas is exemplified by an oxidizing gas such as oxygen and oxygen-containing air. If necessary, a regeneration gas may contain a gas inert on the regeneration treatment, such as nitrogen, carbon dioxide and steam. When there is a risk of acute heat generation by contact of the catalyst with oxygen, it is recommended to add an inert gas to the regeneration gas in order to suppress such an acute heat generation. The temperature for the regeneration treatment is not particularly limited as long as a carbonaceous substance can be removed without thermally deteriorating the catalyst, and is preferably not more than the firing temperature in the catalyst production.

Crude acrolein obtained by the dehydration reaction of glycerin contains by-product. Therefore, it is preferable to purify the obtained crude acrolein. Such a by-product is exemplified by phenol, 1-hydroxyacetone, allyl alcohol and others in addition to propionaldehyde. When crude acrolein is purified, phenol and/or 1-hydroxyaetone is mainly removed. In the production of acrylic acid from acrolein, the yield of acrylic acid is improved by removing the by-product. In particular, when 1-hydroxyacetone is removed, the generation amount of acetic acid can be decreased.

In consideration of improvement of the yield of acrylc acid, it is supposed to be preferable to increase the removal amount of phenol and/or 1-hydroxyacetone. Therefore, both of the mass ratio Ph/A between "A": acrolein and "Ph": phenol after purification and the mass ratio H/A between "A": acrolein and "H": 1-hydroxyacetone after purification are preferably not more than 0.020, more preferably not more than 0.010, and even more preferably not more than 0.005. However, if the removal amount of phenol and/or 1-hydroxyacetone is increased, the loss of acrolein may be increased and purification of acrolein may become troublesome in some cases. From the view of this point, the mass ratio Ph/A and the mass ratio H/A are preferably not less than $1 \times 10^{-9}$, more preferably not less than $1 \times 10^{-7}$, and even more preferably not less than $1 \times 10^{-5}$.

The boiling point of acrolein, phenol and 1-hydroxyacetone are respectively about 53° C., about 182° C. and about 146° C. By use of the boiling point difference, phenol and/or 1-hydroxyacetone can be removed from crude acrolein. The method for removal may be a method of fractional distillation of acrolein having a lower boiling point than the substance to be removed by treating liquid-state crude acrolein in a distillation column; a method of coagulating the substance to be removed having a higher boiling point than acrolein by treating gaseous crude acrolein in a coagulation column; and a method of vaporizing acrolein having a lower boiling point than the substance to be removed by blowing a gas to crude acrolein supplied into a diffusion column.

The melting point of acrolein, phenol and 1-hydroxyacetone are respectively about −87° C., about 43° C. and about −17° C. By use of the melting point difference, phenol and/or 1-hydroxyacetone can be removed from crude acrolein. The method for removal may be a method of cooling crude acrolein and removing precipitates of phenol and/or 1-hydroxyacetone.

In addition, propionaldehyde has a boiling point of about 48° C. and a melting point of about −81° C. It is therefore possible to remove propionaldehyde from crude acrolein by using the difference of the boiling point or melting point from those of acrolein; however, since both of the differences of the boiling point and melting point from those of acrolein are small, loss of acrolein may possibly become large in some cases. Therefore, with respect to propionaldehyde produced in the dehydration reaction, it is preferable that propionaldehyde is not removed from acrolein but is used together with acrolein which is a raw material of acrylic acid.

(2) Method for Producing Acrylic Acid by Oxidation of Acrolein

Acrylic acid can be produced by oxidizing acrolein obtained by the production method as described above.

In the present invention, when glycerin derived from biodiesel is used as a raw material, the obtained crude acrolein may be used for production of acrylic acid without being purified; however, the crude acrolein contains phenol, 1-hydroxyacetone, methoxyacetone, 3-methoxypropanal and the like as by-product. The by-product causes deterioration of catalyst activity and decrease of yield as well as inclusion of by-product such as formic acid, acetic acid, propionic acid, pyruvic acid and 3-methoxypropionic acid in acrylic acid. Therefore, crude acrolein may be used after purification. Such a purification can be carried out by a conventionally known method, and the examples thereof include a method of distilling a coagulated solution of the reaction composition or a collected solution obtained using a collecting solvent and a method using a purifying device equipped with a collecting column or a diffusion column as disclosed in JP2008-115103A. When crude acrolein is not purified, impurity in acrylic acid may be removed by purifying acrylic acid in post-steps. From the viewpoint of simplifying the process and decreasing the production cost, it is preferable to use crude acrolein without purification.

In order to produce acrylic acid, it is preferable to carry out vapor-phase oxidation of acrolein at a temperature of not less than 200° C. and not more than 400° C. in an oxidation reactor by supplying a gas containing acrolein and a catalyst for oxidizing acrolein into the reactor. An oxidation reactor can be arbitrarily selected from a fixed bed reactor, a moving bed reactor, a fluidized bed reactor and the like. Hereinafter, a gas containing acrolein is referred to as "an acrolein-containing gas" and a catalyst for oxidizing acrolein is referred to as "an acrolein-oxidation catalyst" in some cases. Along with oxidation of acrolein, propionic acid is produced from propionaldehyde.

An acrolein-oxidation catalyst is not particularly limited as long as it is a conventionally known acrolein-oxidation catalyst to be used when acrylic acid is produced by gas-phase oxidation of acrolein using molecular state oxygen or a molecular state oxygen-containing gas, and is exemplified by a mixture of a metal oxide and a composite oxide of iron oxide, molybdenum oxide, titanium oxide, vanadium oxide, tungsten oxide, antimony oxide, tin oxide, copper oxide and others. Among the exemplified catalysts, a molybdenum-vanadium-based catalyst containing molybdenum and vanadium as main components is particularly preferable. Further, an acrolein-oxidation catalyst may be a supported catalyst, which contains the above-mentioned mixture or composite oxide of metal oxide on a carrier. The carrier is exemplified by an inorganic oxide and a composite oxide of silica, alumina, zirconia and others, and an inorganic substance such as silicon carbide.

If the amount of oxygen to be added in an acrolein-containing gas for producing acrylic acid is too large, combustion of acrolein may possibly occur in some cases and there is a risk of explosion. Therefore, the upper limit thereof should be properly set.

A gaseous substance containing crude acrylic acid is obtained by a gas-phase oxidation reaction of acrolein. In a collecting step, the gaseous substance is liquefied by cooling condensation or solvent collection to obtain a crude acrylic acid solution. Such a crude acrylic acid solution may be subjected to the crystallization step of the present invention.

Next, a method for producing acrylic acid by using biomass, which is a regenerable resource, is described. There is no direct scheme from biomass to acrylic acid. However, acrylic acid can be prepared relatively easily by dehydrating a hydroxycarboxylic acid such as lactic acid or 3-hydroxypropionic acid. Lactic acid is a natural substance and easily available, and 3-hydroxypropionic acid is produced by decomposing cellulose and the like to obtain a saccharide and further fermenting the saccharide. Hereinafter, lactic acid is referred to as "2-hydroxypropionic acid" or "2HP" and 3-hydroxypropionic acid is referred to as "3HP" in some cases. Acrylic acid can be obtained also by dehydrating a salt of a hydroxycarboxylic acid.

(3) Method for Producing Hydroxypropionic Acid

A hydroxycarboxylic acid and/or a salt thereof can be obtained from various kinds of sources, and it is preferable to use a recyclable biological resource as a carbon source in terms of global warming and environmental preservation. For example, the 2-hydroxypropionic acid derived from a natural substance and the 2-hydroxypropionic acid or 3-hydroxypropionic acid obtained by decomposing cellulose or the like to obtain a saccharide and further fermenting the saccharide can be used.

An aqueous 2-hydroxypropionic acid solution may be obtained by a conventionally known method. For example, the solution can be obtained by fermentation using *lactobacillus* described in Advances in Applied Microbiology, vol. 42, p. 45-95 (1996) or fermentation using mold (*Rhizopus oryzae*) described in Enzyme and Microbial Technology, vol. 26, p. 87-107 (2000).

An aqueous 3-hydroxypropionic acid solution may be also obtained by a conventionally known method. For example, the solution may be obtained by fermentation of glucose as a carbon source using *E. coli* in which a gene of beta-alanine aminotransferase derived from *Streptomyces griseus* ATCC 21897 is introduced, as described in WO2008/027742. Also, the solution may be obtained by fermentation of glucose as a carbon source using *E. coli* in which genes of glycerin dehydrase derived from *Klebsiella pneumoniae* and aldehyde oxydase derived from *E. coli* are introduced, as described WO2001/016346. As the example to obtain an aqueous 3-hydroxypropionic acid solution, the above conventionally known documents are described; however, the microbe or genetically altered microbe used for fermentation is not particularly limited in the methods disclosed in the documents, and any aqueous 3-hydroxypropionic acid solution obtained by fermentation using a living organism having 3-hydroxypropionic acid producibility is usable in the present invention method. In addition, besides fermentation, when an aqueous 3-hydroxypropionic acid solution produced by contacting a saccharide as a raw material with a living organism can be also converted into acrylic acid according to the method described in this specification. In the present invention, the reaction may be carried out using microbe or a treated material derived from a microbe in the presence of a saccharide as a raw material for contacting a saccharide with a living organism. Such a treated material derived from a microbe is exemplified by a fungus body treated with acetone, toluene or the like; a fungus dead body; a freeze-dried fungus body; a crushed fungus body; a cell-free extract of a crushed fungus body; a crude enzyme solution extracted from the fungus bodies; a purified enzyme from the fungus bodies and others. It is also possible to use an aqueous 3-hydroxypropionic acid solution obtained by carrying out the reaction using the above fungus body, the treated material, the enzyme or the like immobilized on a carrier by a common method.

(4) Method for Producing Acrylic Acid by Dehydrating Hydroxypropionic Acid

A conventionally known method may be employed as a method for obtaining crude acrylic acid by dehydrating hydroxypropionic acid. For example, in a method described in JP2005-521718T, an aqueous solution or other solution containing 2- or 3-hydroxycarboxylic acid (2HP or 3HP) or a salt thereof obtained by fermentation and the like is prepared, and the solution is subjected to dehydration reaction by heating the solution in the presence or in the absence of a dehydration catalyst to obtain an unsaturated carboxylic acid or a salt thereof. In the method described in WO2005/095320, an aqueous solution containing 2- or 3-hydroxycarboxylic acid is contacted with an inactive ceramic or a point where an acid or a base solid catalyst is supported at high temperature to produce a 2,3-unsaturated carboxylic acid. In the method described in WO2007/106100, a substance containing a 3-hydroxycarbonyl compound in a substantially liquid state is supplied into a reactor and a conversion reaction is carried out in the reactor to obtain a reaction product containing a 2,3-unsaturated carboxylic acid. In this case, an acid catalyst, a base catalyst or the like is used in the reactor.

According to the above-mentioned methods, a liquid substance or a gaseous substance containing crude acrylic acid can be obtained. Such a liquid substance can be directly used as a crude acrylic acid solution in the present invention. The gaseous substance may be liquefied by cooling condensation or solvent collection in the collecting step to obtain a crude acrylic acid solution. The thus obtained crude acrylic acid solution can be used for the crystallization step of the present invention.

The (meth)acrylic acid produced by the present invention method has stable quality; therefore, when the (meth)acrylic acid is used as a monomer for producing a hydrophilic resin such as a water-absorbing resin or a water-soluble resin, control of a polymerization reaction becomes easy. As a result, quality of the obtained hydrophilic resin is stabilized and various properties of the hydrophilic resin, such as absorption capacity and dispersibility of an inorganic material, are improved. In particular, the acrylic acid produced by the present invention method has stable quality and easy controllability of a polymerization reaction; therefore, the acrylic acid is very useful as a raw material for producing a water-absorbing resin with high water-absorbing capacity and high quality.

Hereinafter, the definition with respect to the water-absorbing resin of the present invention and a preferable embodiment for producing the resin are described.

(1) Water-Absorbing Resin

The term "water-absorbing resin" in the present invention means a water-swellable and water-insoluble polymer gelling material. The term "water-swellable" means that the value of CRC (water-absorption rate under an nonpressurized condition) defined in ERT 441.2-02 is generally not less than 5 g/g, and the term "water-insoluble" means that the value of Ext (water solubles) defined in ERT 470.2-02 is generally not less than 0% by weight and not more than 50% by weight.

The above-described water-absorbing resin can be properly designed in accordance with the use thereof. The water-absorbing resin is not limited, and is preferably a hydrophilic crosslinked polymer obtained by crosslinking polymerization of an unsaturated monomer having a carboxyl group. In addition, it is not necessary that the water-absorbing resin is entirely a polymer (100% by mass), and the resin may contain an additive and the like to an extent that the above-mentioned properties are retained.

In the present invention, the water-absorbing resin may arbitrarily contain a graft component and mainly has acrylic acid and/or a salt thereof as a repeating unit. The term "acrylic acid and/or a salt thereof" is referred to as "acrylic acid (salt)". Specifically, the water-absorbing resin means a polymer containing acrylic acid (salt) in an amount of generally not less than 50% by mole and not more than 100% by mole, preferably not less than 70% by mole and not more than 100% by mole, more preferably not less than 90% by mole and not more than 100% by mole, and even more preferably substantially 100% by mole in the whole monomers (excluding a crosslinking agent) to be used for polymerization.

(2) EDANA and ERT

The term "EDANA" is an abbreviation of European Disposables and Nonwovens Associations, and "ERT" is an abbreviation of a measurement method for water-absorbing resins, EDANA Recommended Test Method, which is the European standard and almost global standard. In the present invention, the physical properties of a water-absorbing resin are measured on the basis of ERT test revised in 2002, unless otherwise specified.

(a) CRC—ERT441.2-02

The term "CRC" is an abbreviation of Centrifuge Retention Capacity and means the water-absorption rate under a nonpressurized condition, which is sometimes referred to as "a water-absorption rate" in some cases. Specifically, the term means a water-absorption rate (unit: g/g) measured by spontaneously swelling a resin in a sodium chloride aqueous solution of 0.9% by weight for 30 minutes and successively dewatering the swollen resin by a centrifuge.

The value of CRC of the water-absorbing resin obtained by the present invention is not less than 20 g/g and not more than 100 g/g, preferably not less than 25 g/g and not more than 50 g/g, and more preferably not less than 27 g/g and not more than 45 g/g.

(b) AAP—ERT442.2-02

The term "AAP" is an abbreviation of Absorption Against Pressure and means a water absorption rate under increased pressure. Specifically, the term generally means the water-absorption rate (unit: g/g) measured after a resin is swollen in a sodium chloride aqueous solution of 0.9% by weight for 1 hour under a load of 2.06 kPa. However, in the present invention, the term means the water-absorption rate (unit: g/g) after a resin is swollen for 1 hour under a load of 4.83 kPa.

The value of AAP of the water-absorbing resin obtained by the present invention is preferably not less than 20 g/g and not more than 30 g/g, and more preferably not less than 22 g/g and not more than 30 g/g.

(c) Ext—ERT470.2-02

The term "Ext" is an abbreviation of Extractables and means water solubles (water-soluble component amount). Specifically, the value thereof (unit: % by mass) is measured by pH titration of the dissolved polymer amount after 1 g of a water-absorbing resin is stirred in 200 g of a sodium chloride aqueous solution of 0.9% by weight at 500 rpm for 16 hours. The Ext value of the water-absorbing resin obtained by the present invention is preferably not less than 0 g/g and not more than 30 g/g, and more preferably not less than 0 g/g and not more than 20 g/g.

(d) FSC—ERT440.2-02

The term "FSC" is an abbreviation of Free Swell Capacity and means a spontaneous swelling rate. Specifically, the term means the water-absorption rate (unit: g/g) measured after 0.20 g of a water-absorbing resin is immersed in a sodium chloride aqueous solution of 0.9% by weight for 30 minutes without being subjected to dewatering by a centrifuge.

(e) Residual Monomers—ERT410.2-02

The term "Residual Monomers (RM)" means the monomer amount remaining in a water-absorbing resin. Specifically, the term means a value (unit: ppm) measured by the following condition. First, 1.0 g of a water-absorbing resin is put in 200 $cm^3$ of a sodium chloride aqueous solution of 0.9% by weight, the mixture is stirred at 500 rpm for 1 hour, and the monomer amount eluted to an aqueous solution is measured by high performance liquid chromatography. The RM value of the water-absorbing resin obtained by the present invention is preferably not more than 1000 ppm and more preferably not more than 500 ppm.

(f) PSD—ERT420.2-02

The term "PSD" is an abbreviation of Particle Size Distribution and means the particle size distribution measured by sieving classification. The weight average particle diameter ($D_{50}$) and the particle diameter distribution width are measured by a method similar to the method described in "(1) Average Particle Diameter and Distribution of Particle Diameter", described in page 7, lines 25 to 43 of EP0349240.

(3) Liquid Permeability

A flow of a liquid flowing among particles of a swollen gel under a load or without a load is called as "liquid permeability". The liquid permeability is measured by SFC (Saline Flow Conductivity) and GBP (Gel Bed Permeability) as representative methods.

The term "SFC (saline flow conductivity)" means the permeability of 0.69% by weight physiological saline through a water-absorbing resin at a load of 0.3 psi, and is measured according to a SFC test method described in U.S. Pat. No. 5,669,894. The unit thereof is [$cm^3 \cdot s \cdot 10^{-7}/g$].

The term "GBP" means the permeability of 0.69% by weight physiological saline through a water-absorbing resin under a load or spontaneous expansion, and is measured according to a GBP test method described in WO2005/016393.

The SFC value of the water-absorbing resin obtained by the present invention is preferably not less than 1 and not less than 5.

(4) Preferable Embodiment for Production

A water-absorbing resin is obtained by crosslinking and polymerizing acrylic acid and/or a salt thereof produced by the present invention method as a main component of monomers with a crosslinking agent using a radical polymerization initiator, and drying and pulverizing the polymerized product. The amount of a crosslinking agent may be not less than about 0.01% by mole and not more than 5% by mole relative to the acrylic acid and/or a salt thereof. The amount of a radical polymerization initiator may be not less than about 0.001% by mole and not more than 2% by mole relative to the acrylic acid and/or a salt thereof.

Preferable examples of a production method in terms of improvement in productivity of the water-absorbing resin are described in U.S. Pat. Nos. 6,867,269, 6,906,159 and 7,091,253, and WO01/038402 and WO2006/034806.

In particular, a method for polymerizing the acrylic acid of the present invention is not particularly limited; however, preferably employable example thereof includes continuous belt polymerization disclosed in U.S. Pat. Nos. 4,893,999, 6,241,928 and US2005/215734; continuous kneader polymerization; and batch kneader polymerization disclosed in U.S. Pat. Nos. 6,987,151 and 6,710,141.

A polymer obtained in the above-mentioned manner is preferably made into a granular water-absorbing resin by a production method disclosed in U.S. Pat. Nos. 4,920,202, 5,264,495, 5,275,773, 6,207,796, 6,164,455, 6,207,796, 6,291,636 and 6,875,511.

It is preferred that a water-absorbing resin is surface-crosslinked in accordance with the intended use or the use application thereof, particularly in the case of using the resin as a sanitary material. The preferable specific method for surface-crosslinking is disclosed in EP0349240, EP0605150, EP0450923, EP0812873, EP0450924, EP0668080, JP7-242709A, JP7-224304A, U.S. Pat. Nos. 5,409,771, 5,597,873, 5,385,983, 5,610,220, 5,633,316, 5,674,633, 5,462,972, WO99/42494, WO9/43720 and WO99/42496.

The above-described documents are incorporated herein by reference.

EXAMPLES

Hereinafter, the present invention is described in detail with Examples. However, the present invention is not limited to the Examples in any way, and it is possible to carry out the present invention according to the Examples with an additional appropriate change within the range of the above description and the following description. Such a change is also included in the technical scope of the present invention.

Example 1

Start of Purification by Crystallization of Acrylic Acid (1) Pretreatment

As the system for supplying a cooling medium and a heating medium to three crystallizers, a system including a refrigerator and buffer tanks was used shown in FIG. 2. The refrigerator could supply three media having respectively different temperatures, and the buffer tank could accumulate the medium which had passed through a crystallizer before the medium was returned to the refrigerator. As the crystallizer, falling film type crystallizers were used. A 40% methanol aqueous solution was used as a refrigerant for the refrigerator. The cross section shape of the buffer tank was a circle with a diameter of 4.0 m, and the height thereof was 17.5 m. A pipe for medium supply was so designed as to mildly supply the medium in order not to impair the temperature gradient due to stirring of the media in the buffer tank when the media was supplied.

First, overall temperatures of two cooling media to be stored in two buffer tanks for cooling medium were adjusted to be −10° C. and −23° C. and overall temperature of a heating medium to be stored in a buffer tank for heating medium was adjusted to be +10° C. using the refrigerator.

(2) Crude Acrylic Acid Solution

Propylene was subjected to a gas-phase catalytic oxidation reaction in a reactor (not illustrated in FIG. 2). The produced reaction gas was supplied into a collection column (not illustrated in FIG. 2) and contacted with a collecting liquid to obtain a crude acrylic acid solution from the bottom of the collection column. The composition of the crude acrylic acid solution was as follows: acrylic acid: 94.3 mass %, water: 2.3 mass %, acetic acid: 2.0 mass %, maleic acid: 0.4 mass %, and other impurities: 1.0 mass %.

(3) Starting Period I

To a first crystallizer to which a cooling medium of −10° C. was supplied at a speed of 22 m$^3$/min, the crude acrylic acid solution (total amount: 86.8 ton) obtained in the above (2) was supplied at a speed of 17 m$^3$/min along a heat transfer face in 30 minutes to crystallize acrylic acid. The temperature of the cooling medium drained from the first crystallizer was increased to 14.5° C. at the maximum; however, the temperature of a cooling medium to be returned to the refrigerator was kept at −6° C. to −4° C. by supplying a cooling medium having a high temperature to the upper part of a buffer tank and draining a cooling medium having a low temperature in the lower part, or mixing a cooling medium having a low temperature drained out of the lower part of the buffer tank with a cooling medium having a high temperature.

In this case, a heating medium of +10° C. was returned to the refrigerator without being cooled, and therefore a heating load was not applied to the refrigerator. However, since only a cooling medium of −10° C. was used for cooling, a cooling load was not so large and the heat generated when a refrigerant for a refrigerator vaporized for cooling a cooling medium was condensed in the refrigerator could be recovered only with cooling water.

As a result, the refrigerator could be operated for 30 minutes to stably supply a cooling medium of −10° C.

(4) Starting Period II

A cooling medium of −10° C. supplied to a first crystallizer was replaced with a cooling medium of −23° C. to further promote crystallization of acrylic acid. At that time, the temperature of the cooling medium after passing through the first crystallizer was increased to 3.8° C. at the maximum; however, a cooling medium to be returned to the refrigerator was kept at −22° C. to −16° C. in the same manner as the above (3). The crystallization in the second stage was carried out for 30 minutes.

A cooling medium of −10° C. was supplied at a speed of 22 m$^3$/min to a second crystallizer and the crude acrylic acid solution obtained in the above (2) was supplied to the second crystallizer in the same manner as the above (3) to crystallize acrylic acid.

In addition, the set temperature of a heating medium at the inlet of the refrigerator was changed from +10° C. to +35° C. with supplying the crude acrylic acid solution to the second crystallizer. As a result, although the temperature of a heating medium to be sent to a buffer tank via a third crystallizer became +35° C., the temperature of a heating medium to be returned to the refrigerator was kept at 30° C. to 32° C. by supplying the heating medium to the upper part of the buffer tank and draining a heating medium to be returned to the refrigerator from the lower part.

In the above-described operation condition, both of cooling media of −10° C. and −23° C. were heated in the crystallizers, and therefore a large cooling load was applied to the refrigerator. However, the cooling load was balanced out since a heating load was applied to the refrigerator for heating a heating medium of 30-32° C. to +35° C. As a result, although only cooling media were actually used, the refrigerator was stably operated and cooling media of −10° C. and −23° C. could be supplied continuously and stably.

(5) Steady Period

A cooling medium of −23° C. supplied to a first crystallizer was replaced with a heating medium of +35° C. to start partial dissolution of an acrylic acid crystal. The surface of the acrylic acid crystal was melted in 10 minutes, and the melted part was discharged out of the crystallizer. Then, heating was continued further 10 minutes to completely melt the acrylic acid crystal. The obtained acrylic acid melted liquid was analyzed; as a result, the purity was 97.9% and the yield was 60.5 ton.

A cooling medium of −10° C. supplied to a second crystallizer was replaced with a cooling medium of −23° C. to further promote crystallization of acrylic acid.

A heating medium of +35° C. supplied to a third crystallizer was replaced with a cooling medium of −10° C. to stabilize the temperature of a heat transfer face at −10° C. Next, the crude acrylic acid solution obtained in the above (2) was supplied to a second crystallizer to crystallize acrylic acid under the same condition as the above (3).

Under the above-mentioned operation condition, both of cooling media and a heating medium were used in crystallizers, and both of a cooling load and a heating load were applied to the refrigerator; therefore, the refrigerator could be stably operated.

Comparative Example 1

Start of Purification by Crystallization of Acrylic Acid

The media were respectively supplied to crystallizers under the same condition as the above Example 1 except that the pretreatment of (1) was not carried out. Specifically, from the beginning, the temperatures of cooling media supplied from the refrigerator were adjusted to be −10° C. and −23° C., and the temperature of a heating medium was adjusted to be +35° C.

The crude acrylic acid solution of Example 1 (2) was supplied to a first crystallizer to which a cooling medium of −10° C. was supplied. As a result, the cooling medium was heated to 14.5° C. at the maximum in the crystallizer and a cooling load was applied to the refrigerator; however, the condensation heat of the gaseous refrigerant generated by the cooling load was recovered by cooling water only.

Next, in the same manner as Example 1(4), a cooling medium of −10° C. and a cooling medium of −23° C. were respectively supplied to a second crystallizer and a first crystallizer to crystallize acrylic acid.

Under the above-described condition, a heating load was not generated, since a heating medium was returned as it was without being cooled; on the other hand, both of cooling media were heated in the crystallizers. Therefore, only a cooling load was applied to the refrigerator, and it became impossible to cool the cooling media to the set temperature. The temperatures of the cooling media to be supplied from the refrigerator respectively became −2° C. and −13° C. at the maximum. As a result, acrylic acid was not cooled sufficiently in the crystallizers. In addition, in the above Example, the time of 30 minutes was enough for crystallization at −10° C. and −23° C. respectively; on the other hand, in Comparative Example 1 in which pretreatment was not carried out, the crystallization time at −20° C. had to be set 60 minutes for sufficient crystallization and thus the entire productivity was lowered. Such a time was two times longer than that of Example 1. Further, the obtained acrylic acid melted liquid was analyzed; as a result, the purity was decreased to 96.2%.

Example 2

Stop of Purification by Crystallization of Acrylic Acid (1) Stopping Period I

After the steady period operation of Example 1(5) was repeated, a stopping procedure was started from a first crystallizer. Specifically, acrylic acid was melted and recovered in the first crystallizer. After the recovery, a heat energy was not required in the first crystallizer. Therefore, a heating medium of +35° C. supplied to the first crystallizer for melting acrylic acid was replaced with a cooling medium of −10° C. after the melting procedure; however, the cooling medium was sent to a buffer tank with keeping the temperature at the outlet temperature of the refrigerator as it was (−10° C.)

A cooling medium of −23° C. supplied to a second crystallizer was replaced with a heating medium of +35° C. to start a sweating procedure and a melting procedure.

In a third crystallizer, a cooling medium of −10° C. was replaced with a cooling medium of −23° C. to further promote crystallization.

Under the above-mentioned operation condition, a cooling medium of −10° C. was not utilized; however, the refrigerator could be operated within the rated level, and a cooling medium of −23° C. and a heating medium of +35° C. could be stably supplied, since both of a cooling load and a heating load were applied to the refrigerator although the loads were not the same.

(2) Stopping Period II

In a second crystallizer, the melted purified acrylic acid was recovered. Next, a cooling medium of −23° C. which came not to be used was supplied to a first crystallizer.

In a third crystallizer, a cooling medium of −23° C. was replaced with a heating medium of +35° C. to start a sweating procedure and a melting procedure.

Under the above-mentioned operation condition, cooling media of −10° C. and −23° C. were not utilized in crystallizers; therefore, the temperatures were not changed even after the media were passed through the crystallizers. On the other hand, a heating medium of +35° C. was cooled in the crystallizer, since the medium had to give heat in the crystallizer. Since the cooled heating medium had to be heated to +35° C. again in the refrigerator, only a heating load was applied to the refrigerator.

Therefore, the temperatures of cooling media to be returned to the refrigerator were set to be lowered. Specifically, the temperatures of −6° C. to −4° C. and −22° C. to −16° C. were respectively decreased to −8.8° C. to −7.6° C. and −22.2 to −20.3° C. As a result, although the cold energy of cooling media were not used in crystallizers, the hot energy stored in buffer tanks was to be used gradually and thus the minimum cooling load was able to be continuously applied to the refrigerator. In this case, the total cooling load on the refrigerator was 20% to 35% of that in a steady state.

As a result, the minimum cooling load was able to be provided continuously to the refrigerator and a heating load on the refrigerator could be balanced out during the sweating procedure and the melting procedure, although only a heating medium was used actually in the crystallizers. Therefore, the refrigerator could be stably operated and a heating medium of +35° C. could be stably supplied. In addition, though it took 40 minutes to obtain a melted liquid of acrylic acid purified through the sweating procedure, the temperatures of cooling media and a heating medium to be returned to the refrigerator could be kept within the predetermined ranges. Such an operation could be carried out within the range of the buffering capacity of the buffer tanks until the melting step was completed.

Comparative Example 2

Stop of Purification by Crystallization of Acrylic Acid

After the same operation as Example 2(1) was carried out, purification by crystallization of acrylic acid was finished in the same manner as Example 2 (2) except that the temperatures of cooling media to be returned to the refrigerator was not adjusted.

Specifically, in the condition of Example 2(2), the temperatures of cooling media to be returned to the refrigerator were respectively kept at −6° C. to −4° C. and −22° C. to −16° C. As a result, after 5 minutes from the start of the melting step in a third crystallizer, cooling media having a relatively high temperature in the buffer tanks for cooling media of −10° C. and −23° C. were consumed, and the temperatures of cooling media to be returned to the refrigerator respectively became −10° C. and −23° C. In other words, a cooling load on the refrigerator was lost. Consequently, the refrigerator could not stably supply a heating medium, and the temperature of the heating medium supplied from the refrigerator was decreased to +10° C. at the lowest.

As a result, the crystallizer could not be sufficiently heated and the acrylic acid crystal was kept as it was in a crystal state in the crystallizer, and thus it took a long time to obtain the melted liquid.

Industrial Applicability

According to the present invention method, in the case of crystallization purification of (meth)acrylic acid by employing a plurality of crystallizers and a refrigerator which can simultaneously supply both of a cooling medium and a heating medium, stable crystallization is made possible and consequently efficient production of (meth)acrylic acid can be maintained even at the start period. In such a start period, although only the cooling medium is used, a cooling medium can be stably supplied. Accordingly, the present invention method contributes to industrial mass production of (meth) acrylic acid, and thus is remarkably industrially useful.

In addition, since the (meth)acrylic acid produced by the present invention method has stable quality, when the (meth) acrylic acid is used as a monomer for producing a hydrophilic resin such as a water-absorbing resin or a water-soluble resin, the control of a polymerization reaction becomes easy, and as a result, the quality of the obtained hydrophilic resin is stabilized and the various properties such as absorption capacity and dispersibility of inorganic ingredient are improved.

Accordingly, the present invention method contributes also to industrial mass production of a hydrophilic resin, and thus is remarkably industrially useful.

The invention claimed is:

1. A method for producing (meth)acrylic acid,
comprising the steps of at least crystallizing (meth)acrylic acid and melting the (meth)acrylic acid crystal obtained in the crystallization step;
wherein:
two or more crystallizers are employed;
(1) when the crystallization step and the melting step are concurrently carried out in separate crystallizers, a cooling medium is supplied to a crystallizer for carrying out the crystallization step to crystallize (meth)acrylic acid and a heating medium is supplied to the other crystallizer for carrying out the melting step to melt the (meth) acrylic acid crystal from a refrigerator; and
(2) when the crystallization step is carried out before the melting step is carried out, the temperature of a heating medium to be returned to the refrigerator is decreased to be lower than a set temperature for the melting step before the crystallization step is carried out.

2. The method according to claim 1, wherein when only the melting step is carried out after completion of the crystallization step, a cooling load on the refrigerator is reduced in comparison with a cooling load for the crystallization step.

3. The method according to claim 1, wherein in (2), before the crystallization step is carried out, the temperature of the heating medium to be returned to the refrigerator is lowered in a range of not less than 5° C. and not more than 35° C. lower than the set temperature for the melting step.

4. The method according to claim 2, wherein when only the melting step is carried out, a cooling load on the refrigerator is set at a range of not less than 10% and not more than 40% of a rated capacity of the refrigerator.

5. The method according to claim 1, further comprising the steps of dehydrating glycerin or β-methylglycerin to obtain (meth)acrolein and oxidating the (meth)acrolein to obtain (meth)acrylic acid.

6. The method according to claim 1, further comprising the step of dehydrating hydroxypropionic acid or 2-methylhydroxypropionic acid to obtain (meth)acrylic acid.

7. A method for producing a hydrophilic resin, comprising the step of polymerizing a monomer component containing (meth)acrylic acid produced by the method according to claim 1.

8. A method for producing a water-absorbing resin, comprising the step of polymerizing a monomer component containing (meth)acrylic acid produced by the method according to claim 1.

9. The method according to claim 2, wherein in (2), before the crystallization step is carried out, the temperature of the heating medium to be returned to the refrigerator is lowered in a range of not less than 5° C. and not more than 35° C. lower than the set temperature for the melting step.

* * * * *